US011185669B2

United States Patent
Aggerholm et al.

(10) Patent No.: US 11,185,669 B2
(45) Date of Patent: Nov. 30, 2021

(54) HIGH STRENGTH BALLOON

(71) Applicant: Cook Medical Technologies LLC, Bloomington, IN (US)

(72) Inventors: Steen Aggerholm, St. Heddinge (DK); Thomas Lysgaard, Solroed Strand (DK)

(73) Assignee: Cook Medical Technologies LLC, Bloomington, IN (US)

( * ) Notice: Subject to any disclaimer, the term of this patent is extended or adjusted under 35 U.S.C. 154(b) by 416 days.

(21) Appl. No.: 15/876,555

(22) Filed: Jan. 22, 2018

(65) Prior Publication Data
US 2018/0140803 A1 May 24, 2018

Related U.S. Application Data

(62) Division of application No. 13/784,028, filed on Mar. 4, 2013, now Pat. No. 9,913,965.

(30) Foreign Application Priority Data

Apr. 13, 2012 (GB) ..................................... 1206541

(51) Int. Cl.
*A61M 25/10* (2013.01)
*A61L 29/04* (2006.01)
(Continued)

(52) U.S. Cl.
CPC .............. *A61M 25/10* (2013.01); *A61L 29/04* (2013.01); *A61L 29/126* (2013.01); *A61L 29/18* (2013.01);
(Continued)

(58) Field of Classification Search
CPC .............. A61M 25/10; A61M 25/1029; A61M 25/1027; A61M 2025/1031; A61M 2025/1075
See application file for complete search history.

(56) References Cited

U.S. PATENT DOCUMENTS 5,669,879 A   9/1997 Duer
5,776,141 A   7/1998 Klein et al.
(Continued)

FOREIGN PATENT DOCUMENTS

CN   102209572 A   10/2011
EP   0 768 097 A2   4/1997
(Continued)

OTHER PUBLICATIONS

International Search Report for corresponding PCT Application No. PCT/US2013/036346, dated Feb. 6, 2014, 4p.
(Continued)

*Primary Examiner* — Jacob T Minskey
*Assistant Examiner* — Adrien J Bernard
(74) *Attorney, Agent, or Firm* — Crowell & Moring LLP

(57) ABSTRACT

A balloon catheter includes a balloon which is both of high strength and radiopaque. The balloon includes an outer strengthened layer which includes a strengthening element at least partially embedded within the layer. Concentrically within the strengthened layer there is a radiopaque layer which includes a high concentration of radiopaque material distributed in the radiopaque layer. The strengthened layer acts as a support to the radiopaque layer which is otherwise be unable to withstand the pressure to which the balloon is normally inflated for deployment and in the course of a medical procedure. The structure provides a high strength radiopaque balloon with a relatively thin balloon wall optimizing balloon flexibility and wrappability. There is also disclosed a method of making a balloon which uses an internal support layer in a raw tubing which is then removed following formation of a balloon.

6 Claims, 3 Drawing Sheets

(51) Int. Cl.
  *A61L 29/12* (2006.01)
  *A61L 29/18* (2006.01)
  *A61M 25/01* (2006.01)

(52) U.S. Cl.
  CPC .... *A61M 25/1027* (2013.01); *A61M 25/1029* (2013.01); *A61M 25/0108* (2013.01); *A61M 2025/1031* (2013.01); *A61M 2025/1075* (2013.01); *A61M 2025/1079* (2013.01); *A61M 2025/1084* (2013.01); *Y10T 29/49826* (2015.01)

(56) References Cited

U.S. PATENT DOCUMENTS

| | | | |
|---|---|---|---|
| 6,258,099 | B1 | 7/2001 | Mareiro et al. |
| 6,652,568 | B1 | 11/2003 | Becker et al. |
| 6,786,889 | B1 | 9/2004 | Musbach et al. |
| 7,824,517 | B2 | 11/2010 | Kampa et al. |
| 2001/0039395 | A1 | 11/2001 | Mareiro et al. |
| 2003/0004535 | A1 | 1/2003 | Musbach et al. |
| 2003/0114915 | A1 | 6/2003 | Mareiro et al. |
| 2008/0157444 | A1 | 7/2008 | Melsheimer |
| 2008/0228025 | A1 | 9/2008 | Quick |
| 2009/0030259 | A1 | 1/2009 | Quick |
| 2009/0306769 | A1 | 12/2009 | Schewe et al. |
| 2010/0234875 | A1 | 9/2010 | Allex et al. |
| 2011/0022152 | A1 | 1/2011 | Grandt |
| 2011/0160661 | A1 | 6/2011 | Elton |
| 2013/0079580 | A1 | 3/2013 | Quick |
| 2013/0190796 | A1 | 7/2013 | Tilson et al. |

FOREIGN PATENT DOCUMENTS

| | | |
|---|---|---|
| JP | 2000-70375 | 3/2000 |
| JP | 2012-507372 | 3/2012 |
| WO | WO 2008/112223 A1 | 9/2008 |
| WO | WO 2009/080320 A1 | 7/2009 |
| WO | WO 2009/148904 A2 | 12/2009 |
| WO | WO 2010/027998 A1 | 3/2010 |
| WO | WO 2010/051488 A1 | 5/2010 |
| WO | WO 2012/009486 A2 | 1/2012 |

OTHER PUBLICATIONS

Communication from EPO with European Search Report and Annex for corresponding European Patent Application No. EP 13 27 5052, dated Aug. 13, 2013, 8p.

Chinese Office Action (second) for corresponding Chinese Application No. CN 201380022797.9 dated Sep. 20, 2016, 7p.

English Language Translation of Chinese Office Action (second) for corresponding Chinese Application No. CN 201380022797.9 dated Sep. 20, 2016, 8p.

Japanese Office Action for corresponding Japanese Application No. JP 2015-505937 dated Nov. 28, 2016, 6p.

English Language translation of Japanese Office Action for corresponding Japanese Application No. JP 2015-505937, 6p.

Japanese Office Action for corresponding Japanese Application No. JP 2015-505937, dated Aug. 1, 2017, Japanese Language, 5p.

English Language translation of Japanese Office Action for corresponding Japanese Application No. JP 2015-505937, dated Aug. 1, 2017, 5p.

Chinese Office Action (first) for corresponding Chinese Application No. CN 201380022797.9, dated Mar. 3, 2016, 6p.

English Language Translation of Chinese Office Action (first) for corresponding Chinese Application No. CN 201380022797.9, dated Mar. 3, 2016, 6p.

HIGH STRENGTH BALLOON

CROSS REFERENCE RELATED APPLICATIONS

This application claims priority to U.S. Non-Provisional Application Serial No. 13/784,028, filed Mar. 4, 2013, and titled "High Strength Balloon", the contents of which are incorporated herein by reference. This application also claims priority to GB application no. 1206541.3, filed Apr. 13, 2012, titled "High Strength Balloon," the contents of which are incorporated herein by reference.

TECHNICAL FIELD

The present invention relates to a balloon catheter for medical applications and in particular a high strength balloon which is readily visible under imaging.

BACKGROUND ART

Balloon catheters, in particular the balloons they carry, are used for a variety of medical applications including: delivery of implantable medical devices such as stents and stent grafts, for vessel dilatation, angioplasty, valvuloplasty and so on. A number of these procedures involves risk to the integrity of the balloon, which can tear or burst as a result of the stresses to which it is put and/or the pressure to which the balloon is inflated. In addition, such balloons, which are typically made from a polymer material for flexibility and compressibility, are virtually invisible under imaging. Lack of visibility of the balloon causes difficulties in controlling the deployment operation. To counter this, it is known to inflate medical balloons with a contrast agent. This does not, however, resolve the lack of visibility of the balloon prior to its inflation. Moreover, contrast media is relatively viscous, leading to lengthened inflation and deflation times, as well as not being particularly biocompatible and thus not ideal in situations where the balloon may burst.

While high strength balloons have been proposed, their structures can be such as to add bulk and lose flexibility, which can lead to reduced wrappability and performance of the balloon.

Examples of prior art balloon catheters are disclosed in US 2011/0160661, EP 0 768 097, U.S. Pat. No. 5,776,141, U.S. Pat. No. 7,824,517 and US 2009/0306769.

DISCLOSURE OF THE INVENTION

The present invention seeks to provide an improved medical balloon and balloon catheter assembly, as well as an improved method of manufacturing a medical balloon and balloon catheter assembly.

According to an aspect of the present invention, there is provided a balloon catheter including a catheter having proximal and distal ends; and a balloon fixed at the distal end of the catheter, the balloon including a plurality of layers superimposed on one another, a first of said layers being a strengthening layer and a second of said layers being a substantially radiopaque layer, the radiopaque layer being positioned inside the strengthening layer and being the innermost balloon layer. The radiopaque layer is advantageously unitary with the strengthening layer.

This structure provides a high strength balloon which has the advantage of good visibility when deployed in a patient. Providing the radiopaque layer internally of the balloon does not compromise the strength of the outer surface of the balloon, and moreover does not risk damage or loss of the radiopaque layer. The structure can also provide for a balloon having a minimal thickness wall, thereby enhancing compressibility/wrappability and flexibility of the balloon.

Advantageously, the strengthening and radiopaque balloon layers are formed of or include a polymer material, preferably the same polymer material. This ensures that these two layers are coupled to one another in a unitary manner.

The radiopaque balloon layer may include a polymer mixed with powder, granules, pellets or fragments of radiopaque material. Preferably, the radiopaque material is or includes tungsten. It has been found that tungsten provides very good radiopacity in relatively small volumes.

Advantageously, the radiopaque balloon layer includes at least 50% by weight of tungsten powder. Embodiments may have 65% or 80% by weight of tungsten powder in the inner layer.

In the preferred embodiment, the strengthening layer includes at least one strengthening element, advantageously being a strengthening sleeve formed of a mesh of filamentary or fibrous material.

The strengthening sleeve is at least partially embedded in a polymer material.

In the preferred embodiment, the strengthening layer forms the outermost layer of the balloon and the balloon is formed of two layers. Thus, the balloon can have a relatively thin wall thickness, contributing to balloon flexibility and wrappability, yet be of high strength and radiopaque at the same time.

According to another aspect of the present invention, there is provided a method of manufacturing a balloon for a balloon catheter, the balloon including a plurality of layers superimposed on one another and having inner and outer balloon surfaces, a first of said layers being a strengthening layer and a second of said layers being a substantially radiopaque layer, the radiopaque layer being positioned inside the strengthening layer and forming the inner balloon layer; the method including the steps of: providing a raw tubing including at least one layer of a polymer material; providing a radiopaque layer inside the layer of raw tubing; providing an expandable support concentrically inside the radiopaque layer; inflating the raw tubing, radiopaque layer and expandable support in a mold so as to form said balloon; and removing the expandable support from the produced balloon.

The method is thus able to produce the balloon in a single process. The inner layer, when heavily radiopaque, is generally too weak to be able to withstand inflation pressure, even during the process of manufacture of the balloon, that is the layer would tear of otherwise disintegrate. The provision of a removable support ensures reliable manufacturing of the balloon without adding to balloon thickness after formation of the balloon.

Preferably, the radiopaque layer is formed integrally with the raw tubing as a multi-layered tubing, for instance by being coextruded with the layer of polymer material.

Advantageously, the method includes the step of providing a strengthening element to said layer of polymer material, the strengthening element being provided in the mold and being attached, bonded to or embedded in the polymer layer on inflation of the raw tubing. Thus, the balloon can be provided with a specific strengthening element, incorporated at the same time as the manufacture by inflation of the balloon from the raw tubing. It is not necessary to apply the strengthening element in a separate and subsequent manufacturing step.

Advantageously, the method includes the step of softening or melting the polymer layer so as to cause the polymer layer to flow around the strengthening element so as to embed at least partially the strengthening element therewithin. The strengthening element can thus be incorporated into the balloon wall by what could be termed a reflow process.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

It is to be understood that the drawings are schematic only and are not to scale. They are of a form which is intended to facilitate the understanding of the teachings herein.

Figure 1:
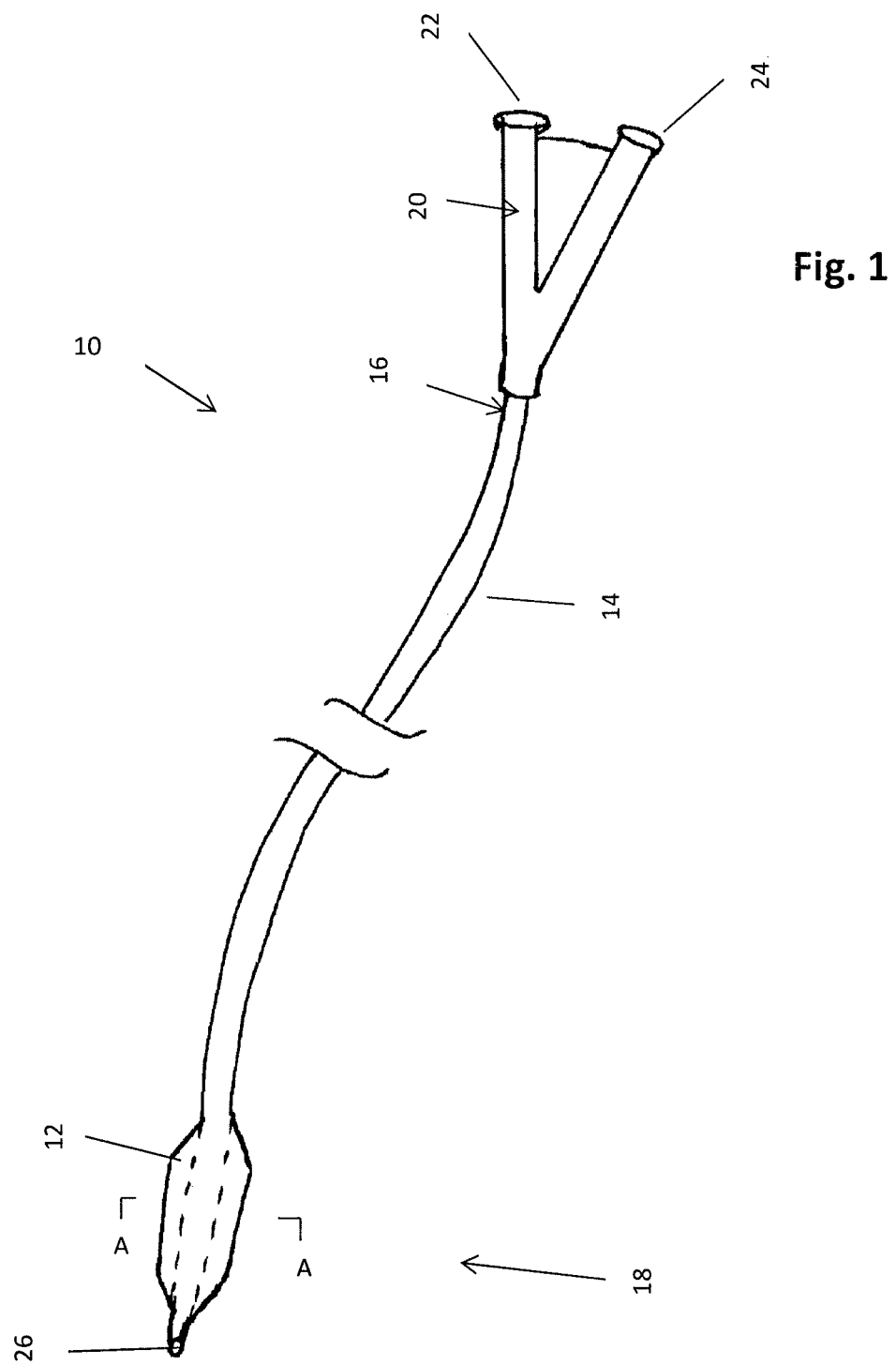
FIG. 1 is a schematic representation of balloon catheter.

Referring to FIG. 1, there is shown in a schematic form the principal components of a balloon catheter assembly 10 which may include a balloon 12 of the type disclosed herein. Catheter assembly 10 includes an elongate tubular catheter 14 having a proximal end 16 and a distal end 18. The balloon 12 is fixed to the distal end 18 of the catheter 14, whereas the proximal end 16 of the catheter 14 is fixed to the handle portion 20, which in the example shown is a Y-connector provided with a first port 22 for a guide wire (not shown) and a second port 24 for the administration of inflation fluid to balloon 12. As is known in the art, catheter 14 includes at least two lumens therein, one coupled to the guide wire 22 and the other to the inflation port 24. The guide wire lumen extends all the way to the tip 26 of the catheter 14, allowing a guide wire to pass through the tip 26 as is known in the art. The lumen for the inflation port 24 extends to an aperture or port (not shown) at the distal end 18, specifically at the zone of the balloon 12 so as to supply inflation fluid to the inside of balloon 12. Typical inflation fluid may be saline solution, a fluid including a contrast medium, as so on.

In FIG. 1 the balloon 12 is shown in an inflated condition, as it would be used in the course of a medical procedure. This may be for the deployment of an implantable medical device which is loaded concentrically on the outside balloon 12, for vascular dilatation, for valvuloplasty, for angioplasty and so on.

The balloon 12 is typically wrapped around the distal end 18 of the catheter 14 for endoluminal delivery through a patient and in this regard the assembly 10, apart from the fitting 20, will be contained within a carrier sheath of known type.

In accordance with the teachings herein, the balloon 12 is a high strength balloon able to withstand higher pressures and greater operating forces compared to equivalent balloons which are not strengthened. Furthermore, the balloon 12 is substantially radiopaque so as to be visible during imaging of the patient in the course of the medical procedure. Yet, the preferred structures disclosed herein provide a balloon 12 of optimum wall thickness so as to retain balloon flexibility as well as good (tight) wrappability around the catheter 12 in order to maintain a small diameter of the introducer assembly and thereby facilitating the deployment procedure.

Figure 2:
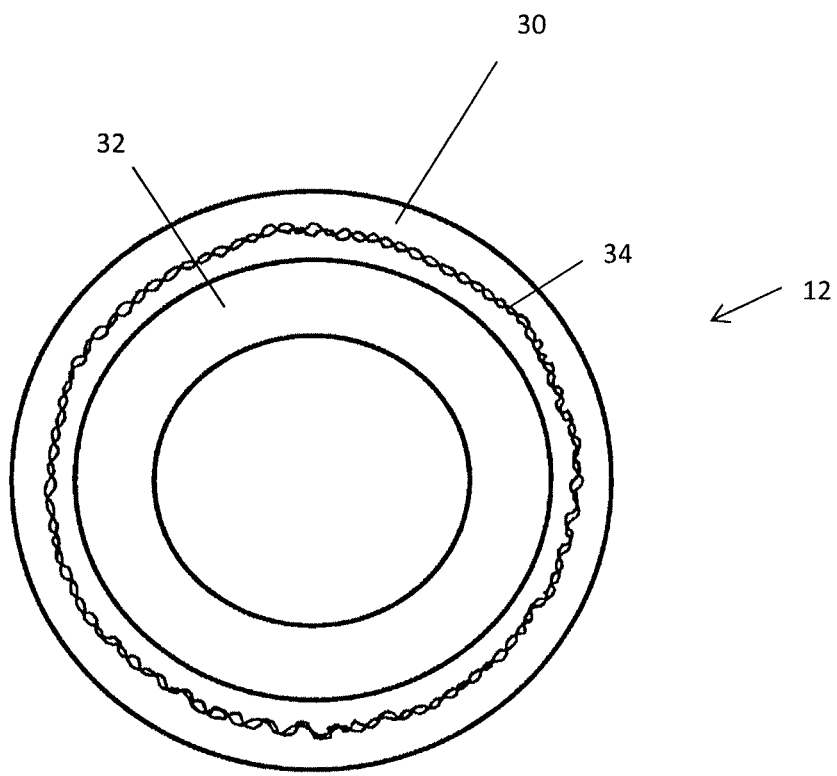
FIG. 2 is a cross sectional view of a first embodiment of balloon structure taken along line A-A of FIG. 1.
Figure 3:
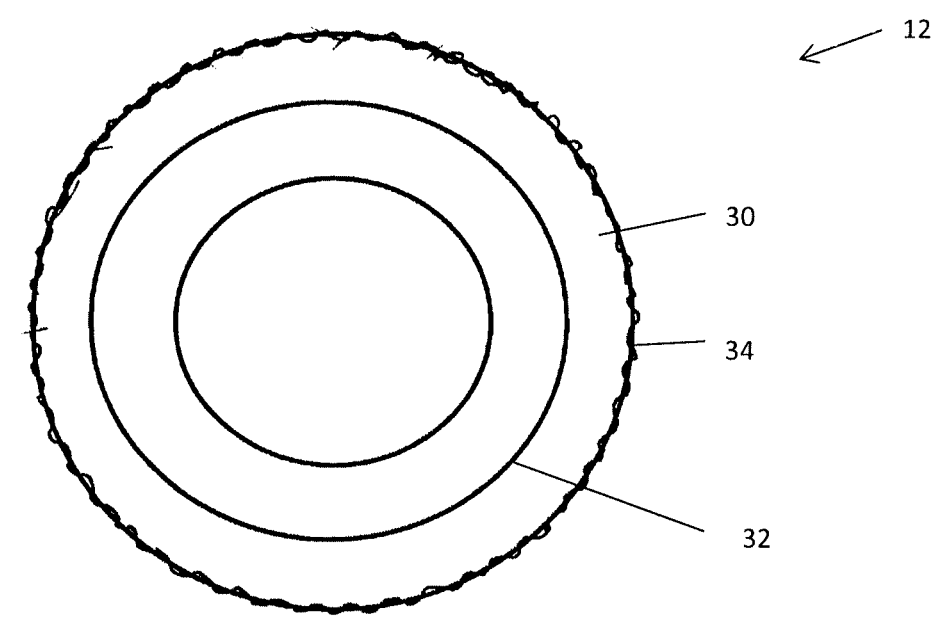
FIG. 3 is a cross sectional view taken along line A-A of FIG. 1 of a second embodiment of balloon structure.

FIGS. 2 and 3 show two embodiments of structure of the balloon 12 of the balloon catheter 10. It is to be understood that these drawings, as with the other drawings of this application, are schematic only and not to scale. In many instances, the features in the drawings are shown enlarged or exaggerated in order to clarify the elements disclosed therein. The skilled person will be readily aware of typical and suitable dimensions for the balloon 12 and the components thereof. For instance, with respect to the embodiments of medical balloon 12 according to the teachings herein, it is to be understood that FIGS. 2 and 3 show structures of balloon walls which are many times thicker than would be used; in practice the layers will be very much thinner. Furthermore, the relative thicknesses of the layers of the balloon 12 shown in embodiments of FIGS. 2 and 3 are not to scale and would differ significantly in an actual balloon. The relative thicknesses of the layers would be dependent upon the material used, the medical application envisaged for the balloon and the arrangement of the various components of the balloon, amongst other factors which will be evident to the person skilled in the art.

Referring first to FIG. 2, the embodiment of balloon 12 shown includes just two layers, an outer strengthened layer 30 and an inner radiopaque layer 32. The outer layer 30 is made of any suitable polymer material including a polyamide such as nylon, a polyether block amide such a PEEBAX, polyurethane or any other suitable polymer, embedded within the outer layer 30 is a strengthening element 34, which in this embodiment is a strengthening sleeve formed of a mesh of fibrous material. The sleeve 34 can be made of any suitable material including polymer, metal or metal alloy, natural fiber; one example being a polyamide such as nylon, ultra-high molecular weight polyethylene fiber such as Dyneema™, as well as graft or suture materials.

In a preferred embodiment, the strengthening sleeve 34 is a woven or knitted mesh of threads, in which the warp and weft fibers extend along the longitudinal and transverse axes of the balloon 12. The strengthening sleeve 34 can have other structures, including a coil extending helically along the balloon 12 or a punctured or apertured sleeve of strengthening material, for instance.

The strengthening element 34 preferably extends along the entire length of the balloon 12, including the generally cylindrical body portion of the balloon and the conical portions either side of the main body portion, preferably up to the necks of the balloon which are attached to the balloon catheter 14. The strengthening element 34 is of a nature that it provides strengthening to the balloon 12 during inflation of the balloon 12, as well as during its medical use.

Internally of the layer 30 is the radiopaque layer 32, which is preferably bonded or otherwise unitary with the strengthened layer 30. The radiopaque layer 32 preferably includes a high proportion of a radiopaque material therewithin. The radiopaque material may be in the form of powder, granules, pellets or fragments dispersed throughout the layer 32. An embodiment provides tungsten powder at a concentration of at least 50% by weight of the layer 32. Tungsten has been found to provide very effective radiopacity even in relatively low amounts, as long as there is sufficient concentration of tungsten. In this regard, other embodiments have greater concentrations of tungsten. Prototypes have been produced with concentrations of tungsten of greater than 65% by weight, up to around 80% by weight.

The radiopaque material, as with layer 32, preferably extends along the whole length of the balloon 12 but at least for the body portion of balloon 12, more preferably along the body portion and the end cone portions and most preferably also along the necks of the balloon which are bonded to the balloon catheter 14.

The remainder of the material forming the inner layer 32 is preferably a polymer material and most preferably the same polymer material as that of the outer layer 30 or a polymer material which has an affinity with the material of the outer layer 30 such that that the two layers 30, 32 bind to one another in essentially a unitary manner. Use of the same or compatible polymers for the inner and outer layers 30, 32 can create a structure in which the two layers are integral with one another and in some cases without any noticeable transition point between the two layers. In other embodiments, where the materials of the inner and outer layers 30, 32 do not naturally bond or integrate with one another, there can be provided a layer of bonding agent which may be a polymer material.

The incorporation of radiopaque material within the inner layer 32, particularly in the form of powder, granules, pellets or fragments and particularly at the concentrations envisaged herein, causes a weakening of the layer 32 compared to a layer made purely of polymer material. More specifically, the embedding of the radiopaque material in the layer 32, particularly in the preferred embodiments, results in the layer 32 being unable to withstand the levels of fluid pressure to which the balloon 12 is subjected during its inflation and during its medical use. In other words, without the provision of a supporting layer such as a layer 30, the inner layer 32 would rupture if subjected to the normal operating pressures of that balloon. It is the outer layer 30 which supports the inner layer 32 during inflation and use of the balloon 12, and which thus prevents the inner layer 32 from rupturing.

FIG. 2 shows the balloon 12 in its simplest and preferable form, that is with just two layers 30, 32 forming the balloon wall. This can provide a structure with a minimal overall balloon wall thickness and thereby which can optimize the flexibility of the balloon 12 as well as its wrappability onto the balloon catheter. It is, of course envisaged that in some embodiments there may be provided additional layers to the balloon 12, for instance in dependence upon the nature of the layers 30, 32 and the medical application intended for the balloon 12. For instance, as described above, there may be provided a bonding layer to bind the two layers 30 and 32 together, there may be provided a texturing layer outside of the layer 30, and so on. Some of these additional layers may add thickness to the overall balloon wall but in return for additional characteristics, features or functions to the balloon 12.

Referring now to FIG. 3, the embodiment of balloon 12' shown in this Figure is very similar to the embodiment of FIG. 2, save for the fact that the strengthening sleeve 34 is only partially embedded within the strengthened layer 30. This may occur when the layer 30 is made particularly thin and thus not thick enough to embed the entirety depth of the strengthening sleeve 34 and/or in cases where it is deemed advantageous to have the strengthening sleeve 34 partially exposed at the outer surface of the balloon 12'. The latter may, for instance, be to provide texturing to the outer surface of the balloon.

Other than the position of the strengthening element 34, the embodiment 30 of FIG. 3 is the same as the embodiment of FIG. 2.

Figure 4:
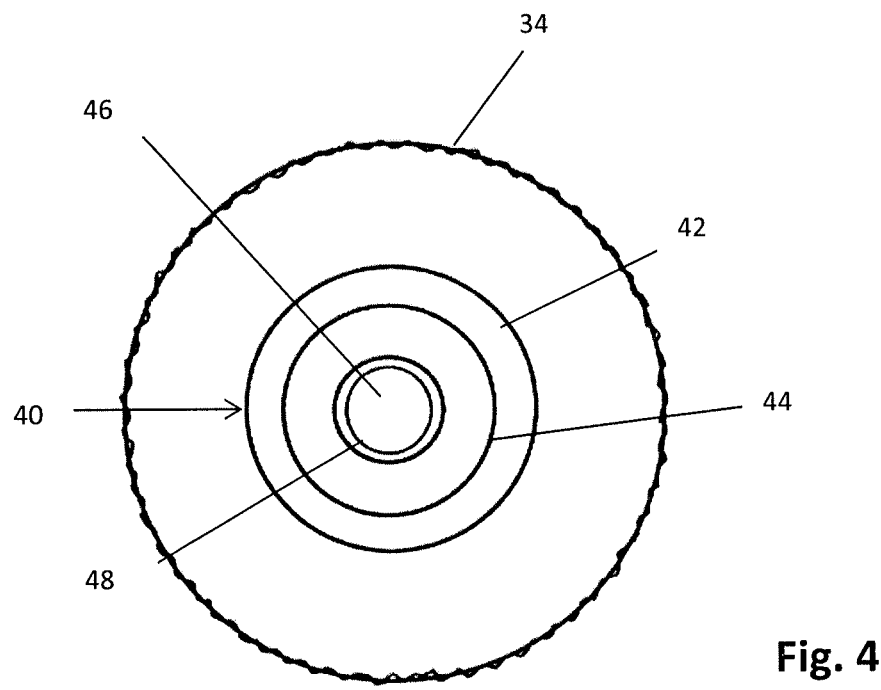
FIG. 4 is an end view of the components used in the manufacture of a balloon having a structure of FIGS. 1 and 3.

Referring now to FIG. 4, there are shown the structural components used in the formation of a balloon 12, 12' of the type shown in FIGS. 2 and 3 and as otherwise taught herein. The balloon is most usefully formed from a raw tubing 40 which in the preferred embodiment is a coextrusion of first and second layers 42, 44. The first, outer, layer 42 is a layer of polymer material which eventually forms outer layer 30 of the balloon 12 or 12'. Inner layer 44 is a layer incorporating radiopaque material which eventually forms the inner layer 32 of the balloon 12, 12'. The inner layer 48 visible in FIG. 4 is described below in connection with the method of manufacture of the balloon for reasons which will become apparent.

Figure 5:
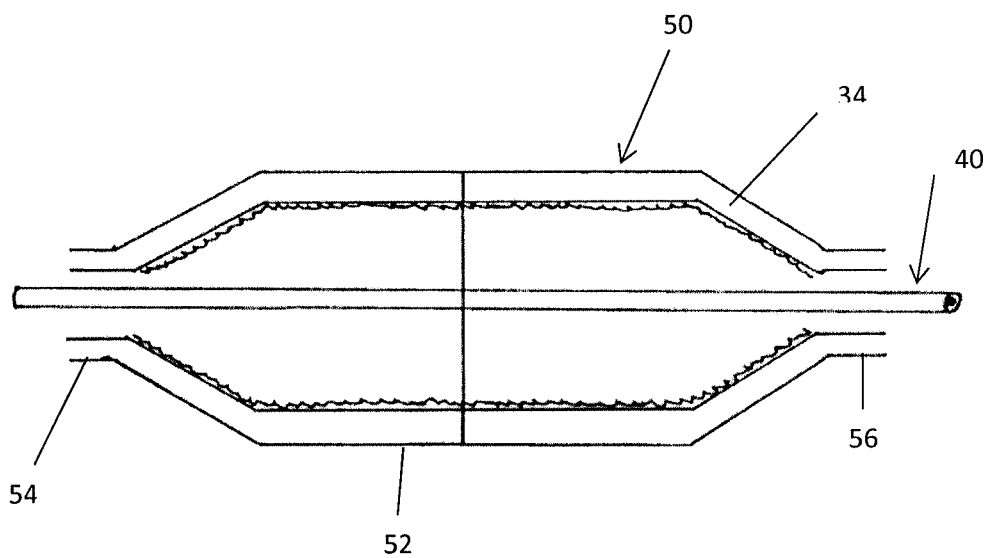
FIG. 5 is a schematic diagram of an example of mold for making a balloon as taught herein.

With reference to FIG. 5, there is shown an example of the mold 50 used for manufacturing a balloon of the type taught herein. The structure of the mold 50 is not relevant to the disclosure in this patent application and can therefore take any of a known number of forms for such molds. Typically, the mold 50 will include a mold chamber 52 which is formed of at least two parts which are separable in order to provide for the removal of a balloon 12 made within the mold 50. The mold also includes inlets or openings 54, 56 designed to grip tightly a raw tubing 40 during the heating and inflation steps of the molding process.

In the preferred embodiment, the balloon 12 or 12' and indeed any other balloon of the type contemplated herein, is preferably formed in a single step process, in which the strengthening sleeve 34 is placed within the mold 50 prior to the inflation of the raw tubing 40. Specifically, the strengthening sleeve 34 is positioned within the mold chamber 52 prior to the insertion of a length of raw tubing 40. The raw tubing is held tightly at the inlet and outlet ports 54, 56 and the end of the tubing 40 at the outlet 54 sealed closed. The mold is then heated and inflation pressure fed into the lumen 46 of the raw tubing 40, this causing the raw tubing 40 to expand radially outwardly.

The raw tubing 40 is heated to a temperature sufficient to cause the outer layer 32 to soften or melt. Thus, as the raw tubing 40 expands under the inflation pressure towards the walls of the chamber 52 of the mold 50, the strengthening sleeve 34 will become embedded, at least partially, within the material 42 and thereby eventually within the outer layer 30 of the subsequently formed balloon.

It will be appreciated that the inner layer 44 of the raw tubing 40 will likewise expand and act to press the outer layer 42 radially outwardly as the result of inflation pressure within the lumen 46. Thus, by a single manufacturing process, the balloon 12 can be formed within the mold 50, in contrast to methods which require subsequent manufacture and assembly steps to form multiple layers and specifically also to attach further components to the formed balloon.

When the concentration of radiopaque material within the layer 44 of the raw tubing 40 is particularly high, it has been found that in some circumstances the inner layer 44 of the raw tubing 40 can fail to expand reliably, leading to the creation of a degraded inner layer 32 to the balloon 12 or 12'. For this purpose, in the preferred embodiment there may be provided an additional layer 48 to the raw tubing 40, this being an innermost layer of the tubing. The layer 48 is used solely during the manufacturing process of the balloon 12, 12' and is removed from within the balloon after the formation thereof. For this purpose, the inner layer 48 may be formed of a material which does not adhere or bond to the radiopaque layer 44, a suitable material being PET.

The internal layer 48 of raw tubing 40 thus acts as a support to the radiopaque layer 44 to ensure the latter remains integral and consistent during the heating and inflation process, thereby to form a uniform and stable internal layer 32 to the balloon, 12'. Once the balloon 12 has been produced, as a result of the lack of adhesion or binding of the internal layer 48 to the material forming the radiopaque layer 32, the layer 48 can simply be peeled off the internal surface of the balloon, plus leaving the radiopaque layer 32 as the innermost layer of the balloon. Once formed, the inner radiopaque layer 32 does not need any further support as it will be supported in effect from the outside in by the strengthened layer 30. Thus, a radiopaque high strength balloon can be produced with minimal wall thickness.

It is to be understood that although tungsten has been described as a preferred radiopaque material, other radiopaque materials may be used including gold, silver, carbon and platinum. A combination may be used.

It is to be understood that the features of the different embodiments described can be combined with one another and that the claims are to be interpreted, even though initially set out in single dependent form, as being combinable as if in multiple dependent form.

What is claimed is:

1. A method of manufacturing a balloon for a balloon catheter, the balloon including a plurality of layers superimposed on one another and having inner and outer balloon surfaces, a first of said layers being a strengthening layer and a second of said layers being a substantially radiopaque layer, the radiopaque layer being positioned inside the strengthening layer; the method including the steps of:

providing a raw tubing including at least one layer of a polymer material, providing a radiopaque layer inside the layer of raw tubing, the radiopaque layer being the innermost layer of the raw tubing, providing an expandable support concentrically inside the radiopaque layer, inflating the raw tubing, radiopaque layer and expandable support in a mold so as to form said balloon, the balloon being formed on an interior surface of the mold, and removing the expandable support from the produced balloon.

2. A method according to claim 1, wherein the radiopaque layer and the strengthening layer are formed together as a unitary layer.

3. A method according to claim 1, wherein the radiopaque layer is formed integrally with the raw tubing as a multi-layered tubing wherein the radiopaque layer and the raw tubing are in contact with each other.

4. A method according to claim 1, wherein the radiopaque layer is coextruded with the layer of polymer material.

5. A method according to claim 1, including the step of providing a strengthening element to said layer of polymer material, said strengthening element being provided in the mold and being attached, bonded to or embedded in the polymer layer on inflation of the raw tubing.

6. A method according to claim 5, including the step of softening or melting the polymer layer so as to cause the polymer layer to flow around the strengthening element so as to embed at least partially the strengthening element therewithin.

\* \* \* \* \*